United States Patent
Feiner et al.

(10) Patent No.: US 6,278,378 B1
(45) Date of Patent: Aug. 21, 2001

(54) PERFORMANCE AND ENTERTAINMENT DEVICE AND METHOD OF USING THE SAME

(75) Inventors: Matthew Feiner, Boston; Michelle Jane Yeeles, Cambridge, both of MA (US); Elizabeth Pierotti, Little Compton, RI (US); Frantz Cadet, Boston, MA (US)

(73) Assignee: Reebok International Ltd., Canton, MA (US)

( * ) Notice: Subject to any disclaimer, the term of this patent is extended or adjusted under 35 U.S.C. 154(b) by 0 days.

(21) Appl. No.: 09/352,784

(22) Filed: Jul. 14, 1999

(51) Int. Cl.[7] ........................................ G08B 5/22
(52) U.S. Cl. ............... 340/815.45; 340/665; 340/691.6; 340/573.1; 36/114; 36/136; 36/137; 362/103; 362/276
(58) Field of Search .................... 340/573.1, 693.5, 340/686.1, 691.6, 665; 482/4, 5, 92, 902; 36/114, 136, 139, 132, 137; 368/10, 9; 362/103, 276

(56) References Cited

U.S. PATENT DOCUMENTS

| | | | | |
|---|---|---|---|---|
| 4,651,446 | * | 3/1987 | Yukawa et al. | 36/132 |
| 4,876,500 | * | 10/1989 | Wu | 324/61 R |
| 5,335,188 | * | 8/1994 | Brisson | 702/163 |
| 5,452,269 | * | 9/1995 | Cherdak | 368/10 |
| 5,471,405 | * | 11/1995 | Marsh | 364/556 |
| 5,483,759 | * | 1/1996 | Silverman | 36/137 |
| 5,775,011 | * | 7/1998 | Reitano, Jr. | 36/136 |
| 5,945,911 | * | 8/1999 | Healy et al. | 340/573.1 |

* cited by examiner

Primary Examiner—Edward Lefkowitz
Assistant Examiner—Davetta W. Goins
(74) Attorney, Agent, or Firm—Sterne, Kessler, Goldstein & Fox PLLC

(57) ABSTRACT

An athletic performance and entertainment device for use on footwear, for example, children shoes. More particularly, an entertainment device which can be attached to the tongue-area of a shoe for providing feedback to a user based on the user's performance during a selected physical activity. The user selects which activity he or she wishes to perform and presses the appropriate function button on the device. The wearer then performs the selected physical activity and the wearer's performance level is indicated by LEDs disposed on the device. A speaker may also be disposed on the device to provide audible feedback to the user. The device keeps track of improvements in performance by promoting the wearer through various award levels as performance increases, until all award levels have been mastered. A novel closure system according to the present invention allows the device of the present invention to be disposed on the tongue of an article of footwear so that the closure system does not obstruct the wearer's view of the device.

24 Claims, 3 Drawing Sheets

PERFORMANCE AND ENTERTAINMENT DEVICE AND METHOD OF USING THE SAME

BACKGROUND OF THE INVENTION

1. Field of the Invention

The present invention relates to a performance and entertainment device for use on footwear, for example, children's shoes. More particularly, the present invention is directed to an entertainment device which can be attached to a shoe for providing feedback to a user based on the user's performance during a selected physical activity.

2. Related Art

Various efforts have been made to incorporate a performance measuring device into an article of footwear for physical therapy and/or athletic training purposes. However, none of these devices have addressed the need, especially in children's footwear, for a performance measuring device which serves the dual purposes of entertainment and performance evaluation.

For example, a foot mounted apparatus for measuring one or more locomotive performance parameters of a person is disclosed in U.S. Pat. No. 5,720,200 to Anderson et al. ("the Anderson Patent"). The Anderson patent discloses an apparatus consisting of a plurality of membrane switches interposed between the user's foot and an underlying surface, preferably within the sole of the footwear. The membrane switches sense the acceleration of the foot when the foot is pushing off from an underlying surface and the deceleration of the foot when the foot is striking against an underlying surface and generate a foot push off signal and a foot strike signal, respectively, in response to such movement. A microprocessor receives the foot push off signal and the foot strike signal and calculates a performance parameter for the person based upon the elapsed time between the signals.

The Anderson patent discloses a calculation and display device, which can be mounted on the tongue of a shoe, for visually and audibly conveying at least one performance parameter to the user. The calculation and display unit has two operating pushbuttons (which function as user input devices) and a display. The calculation and display unit also includes a central processing unit (CPU), a battery and a piezoelectric speaker. The components of the calculation and display unit are encased in a water-proof plastic enclosure that is permanently attached to the upper tongue of the footwear.

The calculation and display unit of the Anderson patent has two operating pushbuttons, one labeled as "Reset/Start" and the other "Function/Select." To activate the device, the user actuates both pushbuttons simultaneously for two seconds to place the calculation and display unit in the function select mode. The desired function is then selected by pressing the function/select button until the display indicates that it is ready to measure the desired performance parameter. The user performs the desired activity and the calculated performance parameter is displayed for one minute or until the function/select pushbutton is used to restart the performance parameter measurement again.

While the Anderson patent is directed to an apparatus and method for providing training information to a user which can be incorporated into different types of footwear, there is a need for a sports performance product, especially for children's shoes, which can be incorporated into different types of footwear to provide performance information to the user in an entertaining form, allowing the user to be awarded for progress and increased performance.

SUMMARY OF THE INVENTION

The present invention is directed to an athletic performance and entertainment product for use on footwear, for example, children shoes. More particularly, an entertainment device is provided that can be attached to the tongue area of a shoe for providing feedback to a user based on the user's performance during a selected physical activity.

The user selects which activity or event he or she wishes to perform and presses the appropriate function button on the device. The wearer then performs the selected event and the wearer's performance level is indicated by LEDs disposed on the device. A speaker may also be disposed on the device to provide audible feedback to the user.

The device keeps track of improvements in performance by promoting the wearer through various award levels as performance increases, until all levels have been mastered. Additional LEDs may be disposed on the device to indicate the wearer's current award level.

A novel closure system according to the present invention allows the device of the present invention to be disposed on the tongue of an article of footwear so that the shoelaces do not obstruct the wearer's view of the device. A tongue shield is disposed over the tongue-area of the article of footwear and a plurality of eyelets and/or ghillie loops are disposed on the backside of the tongue shield, allowing a shoelace to be drawn behind the tongue shield and through the eyelets and/or ghillie loops disposed on the back side thereof. When the shoelace is tied, the knot is disposed behind the tongue shield, securing the article of footwear around the wearer's foot, while at the same time preventing the shoelace from obstructing the wearer's view of the device disposed on the tongue-area thereof. A velcro closure, or the like, between the tongue-area of the article of footwear and the tongue shield may be used to secure the tongue shield and the lace loops and knot to the article of footwear.

BRIEF DESCRIPTION OF THE FIGURES

The foregoing and other features and advantages of the invention will be apparent from the following, more particular description of a preferred embodiment of the invention, as illustrated in the accompanying drawings.

DETAILED DESCRIPTION OF THE PREFERRED EMBODIMENTS

Figure 1:
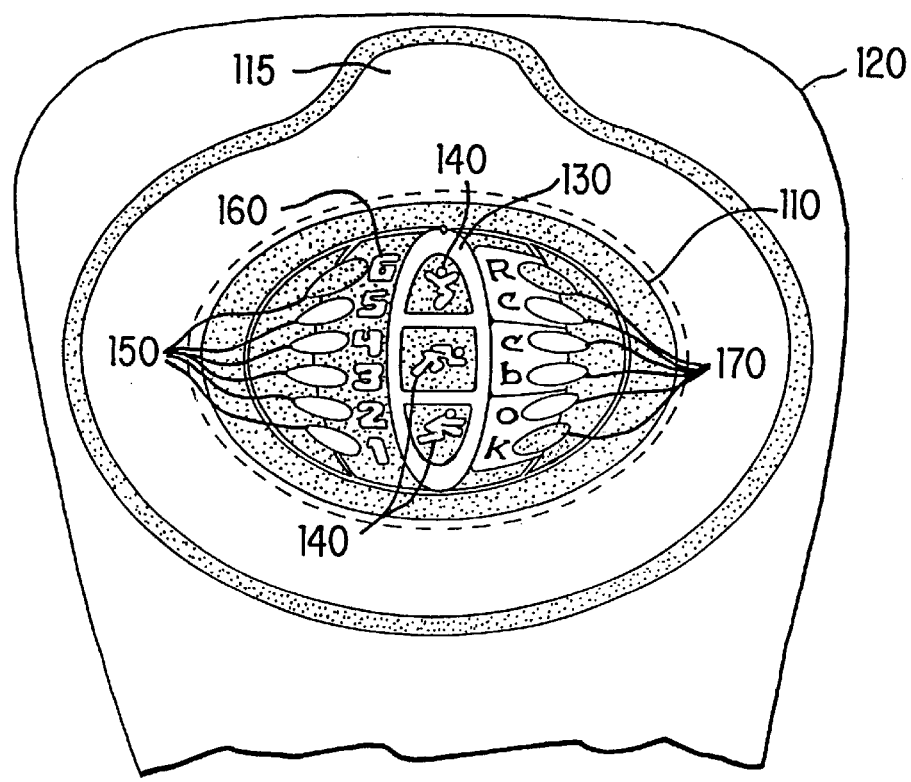
FIG. 1 is a plan view of the device according to the present invention disposed on a tongue-area of an article of footwear.

The present invention relates to an athletic performance and entertainment product, and method of evaluating performance and providing feedback, preferably for use with children's footwear. As shown in FIGS. 1–5, the device is a small pod-like housing 110 which may be permanently sewn onto or otherwise secured to the tongue-area 120 of either a left or right shoe. Alternative shapes for pod 110 which allow pod 110 to be incorporated onto tongue-area 120 can also be used, as would be apparent to one skilled in the relevant art. In the embodiment shown in the figures, the pod is an oval shape. It would be apparent that the pod could be made in a variety of shapes, such as round, triangular, etc.

When using the product according to the present invention, a user, preferably a child, can perform certain physical activities and both see as well as hear the results of his/her efforts. For example, three separate events, such as 1) sprint, 2) high jump, and 3) running long jump can be performed by the user, the user's performance measured, and the results displayed.

Pod 110 preferably consists of a waterproof or water resistant, ultrasonically welded or otherwise sealed, two part acrylonitrile butadiene styrene (ABS) case. Pod 110 could also be made from other similar suitable materials. Although pod 110 is preferably waterproof or water resistant, it is anticipated that the product could be used in environments where it is not a requirement that the product be waterproof or water resistant. The front face of pod 110 (shown in FIG. 1) includes a membrane-like key pad 130 (individual or continuous) consisting of three function buttons 140; each button is dedicated to a particular event (e.g. one for sprint, one for high jump, and one for running long jump). More or fewer function buttons may be provided depending on the desired number of events to be evaluated. The pod 110 is attached to a backboard 115, to provide resistance when a user presses function buttons 140 on pod 110. In one embodiment, backboard 115 is made from a semi-rigid core covered in a fabric material. The semi-rigid core could be made of a thick cardboard, plastic or any other similar semi-rigid material as would be apparent to one skilled in the relevant art.

Figure 2:
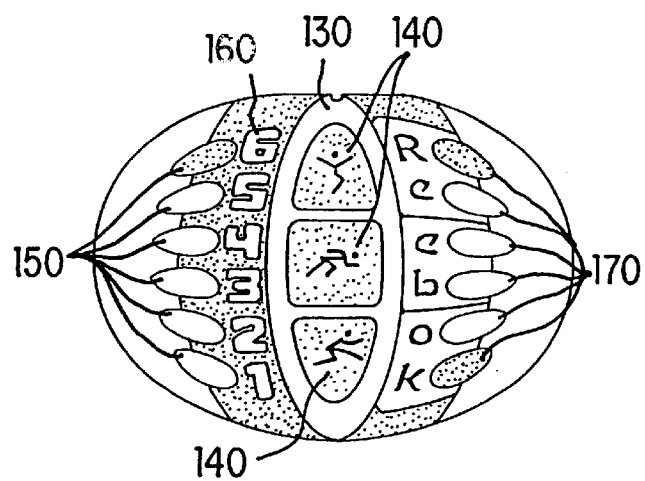
FIG. 2 is a plan view of the device according to the present invention.

Performance results are displayed in the form of colored lights and corresponding sounds. In one embodiment, the front of pod 110 includes 6 performance level indicators 150 vertically aligned along the left side of pod 110 and six award level indicators 170 similarly aligned along the right side of pod 110. Performance level indicators 150 correspond to performance levels 1–6, indicating the level of personal achievement attained by the wearer. Indicators 150 are LEDs and may be of a single color or multiple colors. Performance level descriptors 160, such as the numbers 1–6, as shown in FIG. 2, or level descriptors such as novice, intermediate, advanced, etc. (not shown), are screened onto pod 110 directly next to the corresponding set of performance level indicators 150.

In this embodiment, each award level is divided into six sub-levels, indicated by the six performance level indicators 150 on the device, described above. In one embodiment of the invention, pod 110 may have three award levels (e.g. gold, silver and bronze), indicated by award level indicators 170, such that two adjacent award level indicators 170 are associated with a single award level. It would be apparent that any number of award levels could be used, depending on the desired complexity of the feedback system. Award level indicators 170 are LEDs and may be of a single color or multiple colors.

Pod 110 also includes a speaker (not shown) with a port through the pod case. The port may be covered by a Mylar film, or the like, to maintain the waterproof or water resistant properties of pod 110 and/or the speaker may be sealed directly to the interior of the pod case. The speaker will amplify sounds to a pre-determined acceptable decibel level, such as for use in a playground environment. The speaker will preferably have a preset, non-adjustable sound level; however, it is anticipated that a speaker having an adjustable sound level could be employed without departing from the scope of the present invention. In another alternative embodiment, a user could depress function buttons 140 in a predetermined fashion to mute the sound function.

Figure 3:
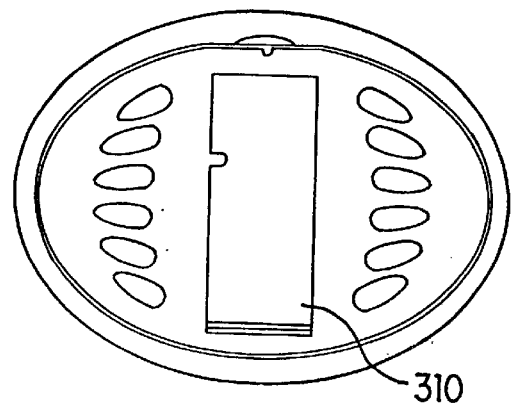
FIG. 3 is a plan view of the inside of the device according to the present invention.

Additionally, pod 110 includes a central processing unit (CPU) 310, as shown in FIG. 3, which contains the electronics necessary to measure the user's performance and to send a signal to indicators 150 and 170 and to the speaker to provide feedback to the user. For example, CPU 310 may be a circuit board having a device for measuring the locomotion of the user, such as an accelerometer, an integrated circuit connected to the measuring device, containing a software program for executing the performance evaluation and feedback operations of the present invention, and a memory device for storing evaluation results. The preferred electronics are available from Personal Electronic Devices, Inc. of Wellesley, Massachusetts. In one embodiment, the power supply for the electronics is provided by a battery.

To use the device, pod 110 must be manually activated by the wearer who decides which physical activity or event he/she wants to perform. The wearer presses the appropriate function button 140 for a specified length of time, preferably for less than 2 seconds. Upon activating the device by pressing any of the three function buttons 140, an event specific sound sequence and light show will play followed by a countdown of sounds and lights. The countdown sound sequence may, for example, include four beeps, similar to the countdown in a drag race. The wearer then performs the selected activity. The wearer will have a set amount of time, for example two seconds, to start the activity. If the user fails to start the activity within two seconds, or if the event is performed incorrectly (e.g. if the sprint requires a run of between 5 and 20 seconds, a run of less than 5 seconds results in a failed attempt), a combination of sounds, such as a "raspberry" sound, indicates to the user that he/she must start over. After a failed attempt signal, the user can press the appropriate function button 140 again for another attempt.

Upon successful completion of any event, a song and scoring sequence of lights will play. The first sound heard is a song indicating that the performance level is being calculated, followed by a count up sound sequence indicating the performance level achieved, followed by an event end song. Additionally, as discussed above, upon successful completion of an activity, performance level indicators 150 are lit to indicate the user's performance level (1–6). If the first level of performance level indicators 150 is lit (corresponding to the number "1"), then the first or lowest level of achievement has been reached; if all six performance level indicators 150 are lit, the highest level of achievement has been reached. Intermediate achievement levels are indicated by illumination of performance level indicators 150 corresponding to levels 2–5. The illumination of performance level indicators 150 and the count up sound sequence are synchronized, in the preferred embodiment, to provide simultaneous audible and visual performance evaluation. A chart, for example a table utilizing a circular slide rule (not shown), can accompany the device to translate the performance level into a universal standard of measurement for each shoe size (inches, feet, or mph, as applicable).

The sound patterns for each performance level can be the same for all three activities. Alternatively, the device can include various combinations of sounds to indicate performance levels. For example, six distinct combinations can be used corresponding to each specific performance level reached. The light show and sound show feedback sequence will cycle, preferably for more than 1 but less than 5 seconds after the activity is completed before the product goes into a sleep mode to prevent battery drain. The product remains is in the sleep mode until one of function buttons 140 is pressed. Additionally, a code can be built in so that parents and teachers can press function buttons 140 in a predetermined fashion to turn off the device. For example, pressing the top two function buttons 140 simultaneously could turn off the device, and pressing the bottom two function buttons 140 simultaneously could return the device to its "on" state.

To view the most recent performance, the wearer manually pushes and holds the appropriate function button 140 for a pre-set amount of time (e.g. three seconds) and the results are displayed. The performance level will be shown by lighting up the appropriate performance level indicators 150 and award level indicators 170 for a specified length of time, for example two seconds. The user can repeatedly recall the most recent performance for each of the three events. The last successful completion will remain in memory until a new successful completion for each of the three events. All performance and award levels can be reset by holding down all three function buttons simultaneously for a specified length of time, for example, three seconds, to clear the most recent results.

The award indication aspect of the device is based on a graduation concept. The user selects the activity to be performed by pressing one of function buttons 140. Then, pod 110 prompts the user to perform the desired event. Upon completion of the event, the device calculates the user's performance and displays the results. When the wearer meets a preset performance standard, the user progresses to the next award level, until the user has mastered all award levels. As the award level increases, the performance standard required to achieve the highest performance level may also increase, so that the mastery of higher award levels is more challenging. As discussed above, pod 110 may have three award levels (e.g. gold, silver, and bronze), indicated by award level indicators 170, such that a pair of adjacent indicators 170 are associated with each award level.

When the user first activates the device, the award level is set to its lowest level, e.g., bronze. The user must achieve the highest performance level rating (e.g., 6) in a given event during a specified number of trials, either consecutively or non-consecutively, to "master" the current award level and graduate to the next award level (e.g., silver). The user progresses until all award levels are mastered. In one embodiment, the user must achieve the highest performance level rating, indicated by the lighting of all six performance level indicators 150, during three separate trials in a given award level in order to graduate to the next award level. The graduation from one award level to the next is displayed using a light show and a graduation song. For example, upon graduation, the "Pomp and Circumstance" theme song may be played and a corresponding light pattern is displayed. During the song, illumination of award level indicators 170 will move up from the current award level to the new award level. Pod 110 stores the most recent award level achieved for each event, unless the performance levels are reset, as discussed above. Thus, the user is allowed to make numerous attempts to master all award levels. Upon mastering the gold award level, a specific "mastery" light show and song, for example, the "Mexican Hat Dance" theme, will play. Thereafter, there is no further graduation.

EXAMPLE 1

In this example, the user activates the device by pressing the function button 140 for the activity desired, for example high jump. Pod 110 is set to its lowest award level, for example, the bronze award level, indicated by the lighting of the bottom-most pair of award level indicators 170 corresponding to the bronze award level. Pod 110 prompts the user to perform the desired activity. After the high jump is performed, the device calculates the user's performance and displays the results. If the highest level of performance is achieved for the bronze award level, all six performance level indicators 150 light up. If the highest level is achieved during three separate trials, the award level is incremented from the bronze award level to the silver award level, indicated by the lighting of the middle pair of award level indicators 170, corresponding to the silver award level, and playing of the graduation song. Likewise, after achieving the highest performance level in the silver award level during three separate trials, the user progresses to the gold award level, indicated by the lighting of the topmost pair of award level indicators 170, corresponding to the gold award level. Finally after achieving the highest performance level in the gold award level during three separate trials, the "mastery" sound and light show is displayed to indicate that the user has mastered all award levels. As the award level increases, the performance standard required to achieve the highest performance level may also increase, so that the mastery of higher award levels is more challenging.

In one embodiment, an Internet website can be maintained in connection with the device, to provide more information about the performance evaluation and feedback features of the device as well as games and other information of interest to wearers of the device. Additionally, a computer interface, such as a serial port (not shown), can be disposed on the device to allow the user to download performance results to the website, to be ranked against others, or to upload new performance criteria from the web site to the device, adding further flexibility to the device.

Figure 4:
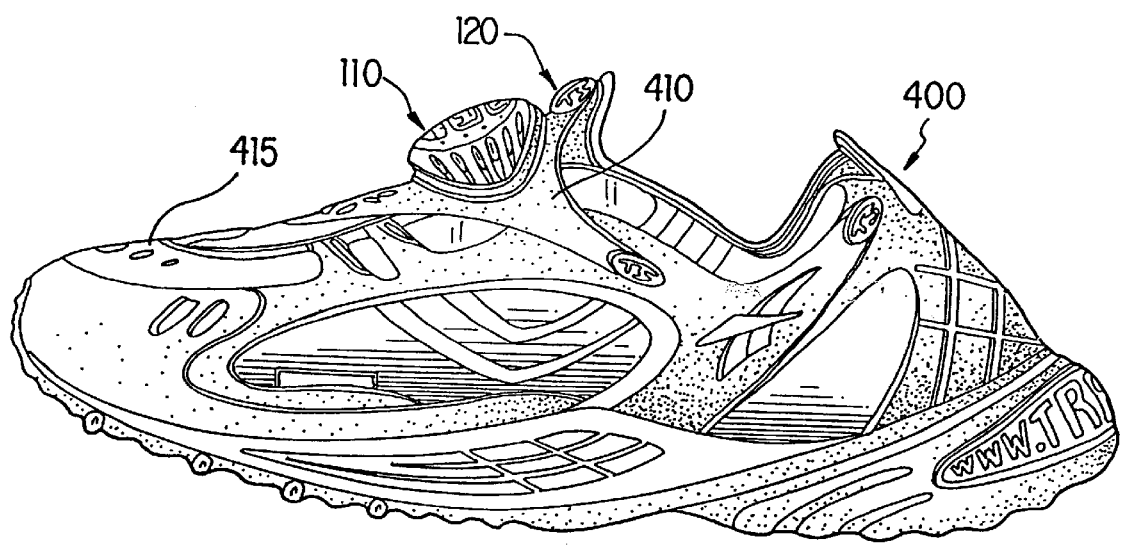
FIG. 4 is a side view of a shoe according to the present invention.
Figure 5:
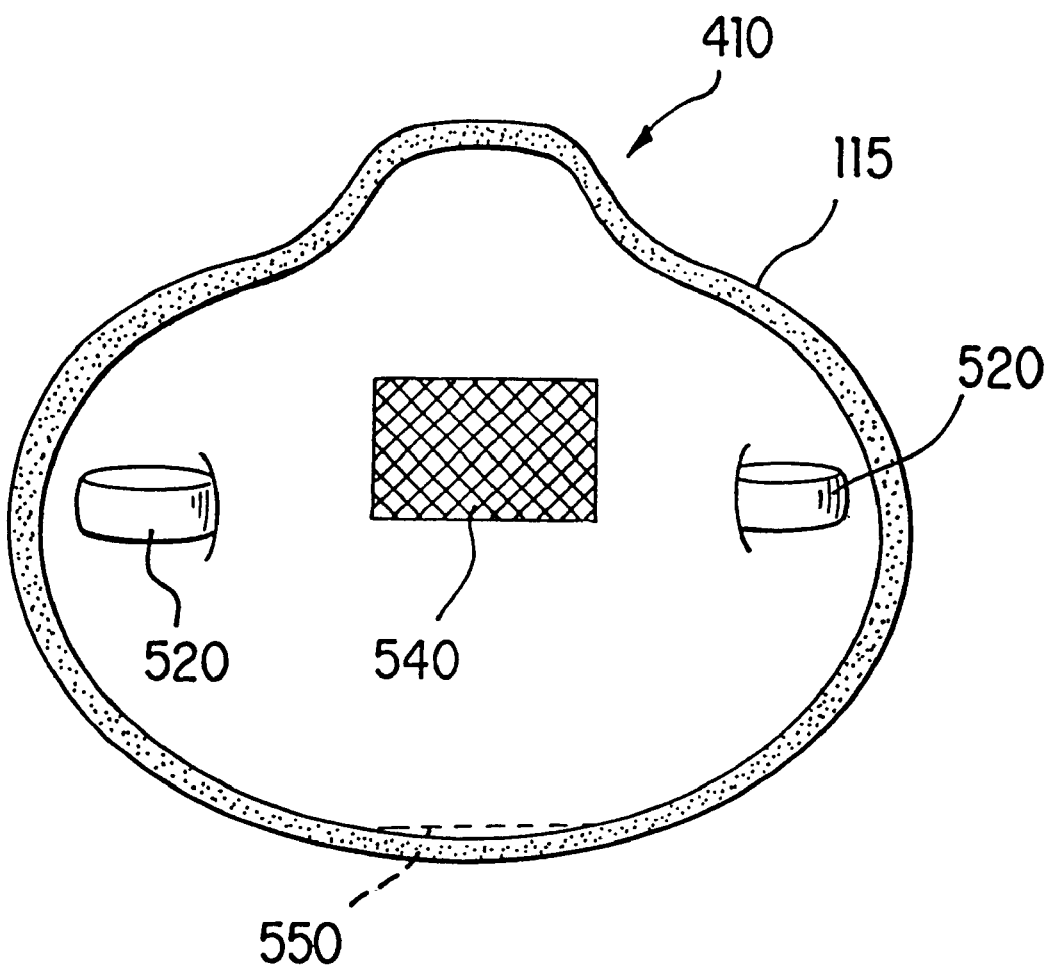
FIG. 5 is a rear plan view of the tongue shield according to the present invention.

To enable pod 110 of the present invention to be disposed on the tongue-area 120 of either a left or right shoe, one embodiment of the present invention utilizes a novel lacing system. As shown in FIG. 4, a tongue shield 410 is secured to an upper 415 of a shoe 400 and lays over tongue area 120 of shoe 400. Tongue shield 410 includes backboard 115 and pod 110. As shown in FIG. 5, plurality of eyelets and/or ghillie loops 520, preferably two, are disposed on the backside of tongue shield 410, allowing a pair of shoelaces (not shown) to be drawn behind tongue shield 410 through eyelets and/or ghillie loops 520. In this manner, a shoe incorporating pod 110 of the present invention can be laced without the shoelaces interfering with the wearer's ability to access and view pod 110. For example, the shoelaces can be strung along the vamp of the shoe as is conventional in the art. Then, the shoelaces can be strung behind tongue shield 410 and through the last set of eyelets or ghillie loops 520 disposed on the backside of tongue shield 410. The shoelaces are then tied so that a knot is disposed behind tongue shield 410. Tongue shield 410, loops 520 and the knot can be further secured to tongue-area 120 through a hook-and-pile type closure, or the like. One half 540 of the hook-and-pile closure is shown disposed on the back of tongue shield 410. The other half (not shown) would be disposed on the tongue area 120 of shoe 400. Tongue shield 410 could be further secured to tongue area 120 by stitching 550, as shown in FIG. 5. This novel lacing system allows the shoe to be secured around the wearer's foot, while at the same time preventing the shoelaces from obstructing pod 110. While the pod of the present invention is permanently attached to the shoe, it is anticipated that pods could be detachably secured, and further, that pods could be sold separately as after-market devices, without departing from the scope of the present invention.

Through the novel user interface, feedback system and graduation concept described above, the device of the present invention solves the need for a sports performance product, especially for children's shoes, which can be incorporated into different types of footwear to provide performance information to the user in an entertaining form, allowing the user to be awarded for progress and increased performance. The novel lacing system of the present invention allows the sports performance product of the present invention to be easily incorporated onto a typical athletic shoe, without sacrificing the fit of the shoe.

While the invention has been particularly shown and described with reference to preferred embodiment thereof, it will be understood by those skilled in the art that various changes in form and details may be made therein without departing from the spirit and scope of the invention. For example, a voice activated user interface, wherein the user no longer has to push function buttons 140 to initiate a particular event, could be used without departing from the scope of the present invention. Additionally, it would be apparent to one skilled in the relevant art that the LEDs of indicators 150 and 170 could be replaced with an LCD or similar display device. The LCD device could also be equipped to provide a readout (inches, feet, or mph, as applicable) to translate the current performance level into a universal standard of measurement, corresponding to the conversion chart discussed above. Alternatively, the device itself could be the performance level indicator, such that the device changes color based on the user's performance. For example, pod 110 could be provided with Chromacore™ technology, available from Color Kinetics Incorporated, Boston, Mass. Additionally, the count up sound sequence could be replace with a digitized voice to provide "human" feedback. For example, the digitized voice could tell the wearer "You ran six miles per hour, not bad."

While the preferred embodiment of the present invention was directed to the evaluation of specific athletic activities, sprint, high jump, and running long jump, it could also be used to evaluate other athletic activities without departing from the scope of the present invention. For example, the device could evaluate the user while running races of various distances (500 meter, 1000 meter, etc.). Alternatively, the device could be disposed on a shoe such as a soccer shoe to indicate how hard a wearer kicked a ball. The measurement would be in terms of PSI rather than distance. Alternatively, the device could be programmed as a "Simon says" game, in which the device instructs the user to "jump forward, jump right, run left, and jump up," or to "jump up three times." The device would then be able to assess whether the user followed the instructions. The commands could be offered via a digitized voice or specific sound/light codes.

Also, while the present invention is directed to an athletic performance device, it could also be used to evaluate performance and provide feedback for non-athletic activities without departing from the scope of the invention. For example, it could be used to evaluate musical performance, such as singing, wherein the user is required to sing a particular note and the device evaluates pitch, sustain, volume, etc. to produce a performance level. As the user progresses through the various award levels, the octave is increased or decreased to provide further difficulty for the user.

Similarly, the present invention could be incorporated into a game device, such as a device that allows the user to play tag. In a freeze tag embodiment, once the wearer is tagged, he or she must press a button on the device. The device then counts down for a preset time period, e.g., 30 seconds. The wearer must remain "frozen" during the count down. Once the count down is complete, the wearer can move. The winner is the person who can "freeze" the entire team at the same time. In a laser tag embodiment, the device acts as a receiver for lights signals emitted from a "laser" device, such as a toy laser gun. Upon sensing the light signals, the device indicates that the wearer has been "tagged." The device can then count down, as described above for the freeze tag embodiment, during which time the wearer remains tagged or out of the game. Once the count down is complete, the wearer is allowed back in the game.

Similarly, additional electronics can be disposed in the device of the present invention to allow for additional uses. For example, a digital camera could be disposed on the device, allowing the wearer to take photographs via their shoe. Alternatively, an RF transmitter could be disposed in the device. For example, in an alternate embodiment, the device can contain a chip that sends a signal to a remote receiver as the wearer passes the receiver location. The remote receiver could be a kiosk at a designated location, for example, at a theme park. The theme park would offer the wearer free admission, a special prize or a discount upon sensing that the wearer has the device on their shoe. Alternatively, the transmitter could be used to locate the wearer, in a process similar to that used in the Lojack system for cars. For example, a parent, having a compatible receiver, could track down a lost child wearing shoes having a device according to the present invention with the transmitter chip. In an alternative embodiment, an RF receiver can be disposed in the device along with the RF transmitter, allowing signals to be sent and received by devices according to the present invention on different wearer's shoes. For example, in a race, the transmitted signals can be evaluated by the device to produce an audible signal corresponding to the proximity of the other contestants. As a competitor racing behind the wearer gets closer to the wearer, the device makes louder, higher pitched sounds. Various other changes in form and application of the present invention would be apparent to one skilled in the relevant art.

What is claimed is:

1. A performance and entertainment device, comprising:
   a housing;
   a central processing unit disposed within said housing;
   a switch disposed on said housing and connected to said central processing unit for providing input to said central processing unit; and
   a display device connected to said central processing unit for receiving output from said central processing unit, wherein said central processing unit is capable of producing a performance level evaluation for a user of the device during at least one physical activity, providing performance feedback to the user based on comparing the performance level evaluation with a preset performance criteria for a current award level and automatically varying said current award level in response to said performance level evaluation, such that said current award level is increased to a new award level in response to an improvement in the user's performance, resulting in increased preset performance criteria corresponding to said new award level.

2. A device according to claim 1, wherein said housing is attached to a tongue area of an article of footwear.

3. A device according to claim 1, further comprising a speaker disposed within said housing for receiving output from said central processing unit.

4. A device according to claim 1, wherein said switch is activated by engagement of a function button.

5. A device according to claim 1, wherein said display device comprises an LED.

6. A device according to claim 1, wherein said housing is water resistant.

7. A device according to claim 1, wherein said housing comprises a sealed two part plastic case.

8. A device according to claim 1, wherein said central processing unit is capable of evaluating a wearer's performance in a physical activity taken from the group of physical activities consisting of at least one of the following: sprint, high jump or running long jump.

9. A device according to claim 1, wherein said preset performance criteria require achieving a maximum performance level for the current award level during each of a plurality of performances.

10. A device according to claim 1, wherein said current award level is increased when the user meets a predetermined performance standard, until all award levels have been mastered.

11. A device according to claim 10, wherein said performance standard increases as said current award level increases.

12. A device according to claim 1, further comprising a memory for separately storing the performance level evaluation and current award level for each activity performed.

13. A method of evaluating performance and providing feedback comprising the steps of:

(a) selecting a physical activity to be performed;

(b) evaluating the performance of the activity for a current award level;

(c) displaying the activity performance level evaluation; and (d) if the activity performance level evaluation exceeds a preset performance criteria for said current award level, automatically increasing said current award level to award level in response to an improvement in the user's performance, resulting in increased preset performance criteria corresponding to said new award level.

14. A method according to claim 13, further comprising the step of audibly conveying the activity performance level evaluation.

15. A method according to claim 13, wherein said selecting step comprises selecting an activity to be performed from a plurality of different activities consisting of at least one of the following: sprint, high jump or running long jump.

16. A method according to claim 15, wherein said selecting step comprises selecting an activity to be performed by activating a switch.

17. A method according to claim 16, wherein said switch is actuated by engagement of a function button.

18. A method according to claim 13, wherein said steps (b), (c), and (d) are performed by a microprocessor incorporated into a module and said step (a) is performed by a user of the module.

19. A method according to claim 13, wherein said displaying step comprises displaying the activity performance level evaluation by activating an LED.

20. A method according to claim 13, wherein said preselected performance criteria requires achieving a maximum performance level for the current award level during each of a plurality of performances.

21. A method according to claim 13, further comprising the step of separately storing the activity performance level evaluation and current award level for each activity performed.

22. A method according to claim 13, wherein said current performance and award level can be reset.

23. A method according to claim 13, wherein said step (d) further comprises increasing the current award level when the user meets a predetermined performance standard, until all award levels have been mastered.

24. A method according to clam 23, wherein said step (d) further comprises increasing said performance standard as said current award level increases.

* * * * *